(12) United States Patent
Danelski et al.

(10) Patent No.: US 11,993,502 B2
(45) Date of Patent: May 28, 2024

(54) DEVICE AND METHOD FOR TREATING CONTAINERS

(71) Applicant: KHS GMBH, Dortmund (DE)

(72) Inventors: Alexander Danelski, Bad Kreuznach (DE); Jan Leyendecker, Schmelz (DE); Thomas Niehr, Bad Muenster am Stein Ebernburg (DE)

(73) Assignee: KHS GmbH, Dortmund (DE)

( * ) Notice: Subject to any disclaimer, the term of this patent is extended or adjusted under 35 U.S.C. 154(b) by 187 days.

(21) Appl. No.: 17/778,513

(22) PCT Filed: Nov. 11, 2020

(86) PCT No.: PCT/EP2020/081736
§ 371 (c)(1),
(2) Date: May 20, 2022

(87) PCT Pub. No.: WO2021/099192
PCT Pub. Date: May 27, 2021

(65) Prior Publication Data
US 2023/0002209 A1    Jan. 5, 2023

(30) Foreign Application Priority Data
Nov. 21, 2019   (DE) ............... 10 2019 131 494.1

(51) Int. Cl.
*B67C 7/00*          (2006.01)
(52) U.S. Cl.
CPC ...... *B67C 7/0033* (2013.01); *B67C 2007/006* (2013.01)

(58) Field of Classification Search
CPC .......... B67C 7/00; B67C 3/22; B67C 7/0073; B67C 2007/006; B67C 2003/228; B67C 3/2642; B67C 3/26; B67C 3/007
(Continued)

(56) References Cited

U.S. PATENT DOCUMENTS 8,844,585 B2   9/2014  Laumer et al.
9,205,985 B2  12/2015  Niehr et al.
(Continued)

FOREIGN PATENT DOCUMENTS

CN   102372242 A   3/2012
CN   107108059 A   8/2017
(Continued)

*Primary Examiner* — Jacob A Smith
(74) *Attorney, Agent, or Firm* — Laurence A. Greenberg; Werner H. Stemer; Ralph E. Locher

(57) ABSTRACT

In an apparatus for treating containers with a medium, the containers are transported cyclically in groups. A linear holding device has a plurality of container holders for holding the containers in a suspended state. A treatment device has a plurality of outlet heads that are connected to a supply line for the medium via respective branch lines. The outlet heads are moved together as a group in the vertical direction. Each outlet head has an outlet line for discharging the medium into the containers. For the purpose of treating the container, the outlet line is introduced into the container, which is held in a suspended state in the container mount. Each outlet head is assigned a controllable restraining mechanism. A controller communicates with the restraining mechanism to control a restraining element to hold back the outlet line of a respective outlet head in a restraining position as required.

20 Claims, 7 Drawing Sheets

(58) Field of Classification Search
USPC .......................................................... 53/426
See application file for complete search history.

(56) References Cited

U.S. PATENT DOCUMENTS

| | | | |
|---|---|---|---|
| 10,787,285 B2 | 9/2020 | Linnestad | |
| 11,498,707 B2 | 11/2022 | Strauss | |
| 2009/0130268 A1* | 5/2009 | Euler | .................... B67C 3/007 |
| | | | 426/232 |
| 2020/0346879 A1 | 11/2020 | Niehr et al. | |

FOREIGN PATENT DOCUMENTS

| | | | | |
|---|---|---|---|---|
| CN | 109311542 A | 2/2019 | | |
| DE | 10045064 A1 | 3/2002 | | |
| DE | 202018104454 U1 | 8/2018 | | |
| DE | 102017127322 A1 | 5/2019 | | |
| EP | 2599721 A2 | 6/2013 | | |
| FR | 748104 A | 6/1933 | | |
| GB | 1233688 A | 5/1971 | | |
| WO | 0128863 A1 | 4/2001 | | |
| WO | WO-0128863 A1 * | 4/2001 | .............. | A61L 2/22 |
| WO | 2013004324 A1 | 1/2013 | | |

\* cited by examiner

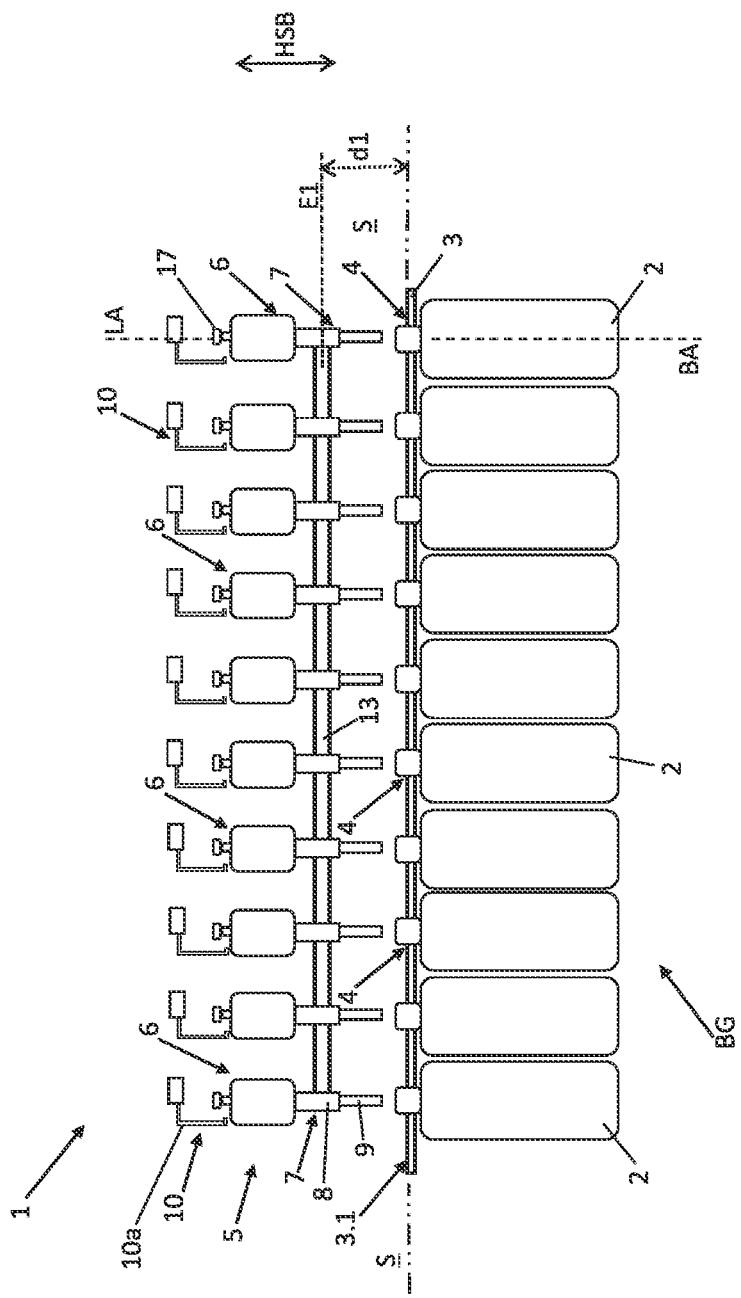

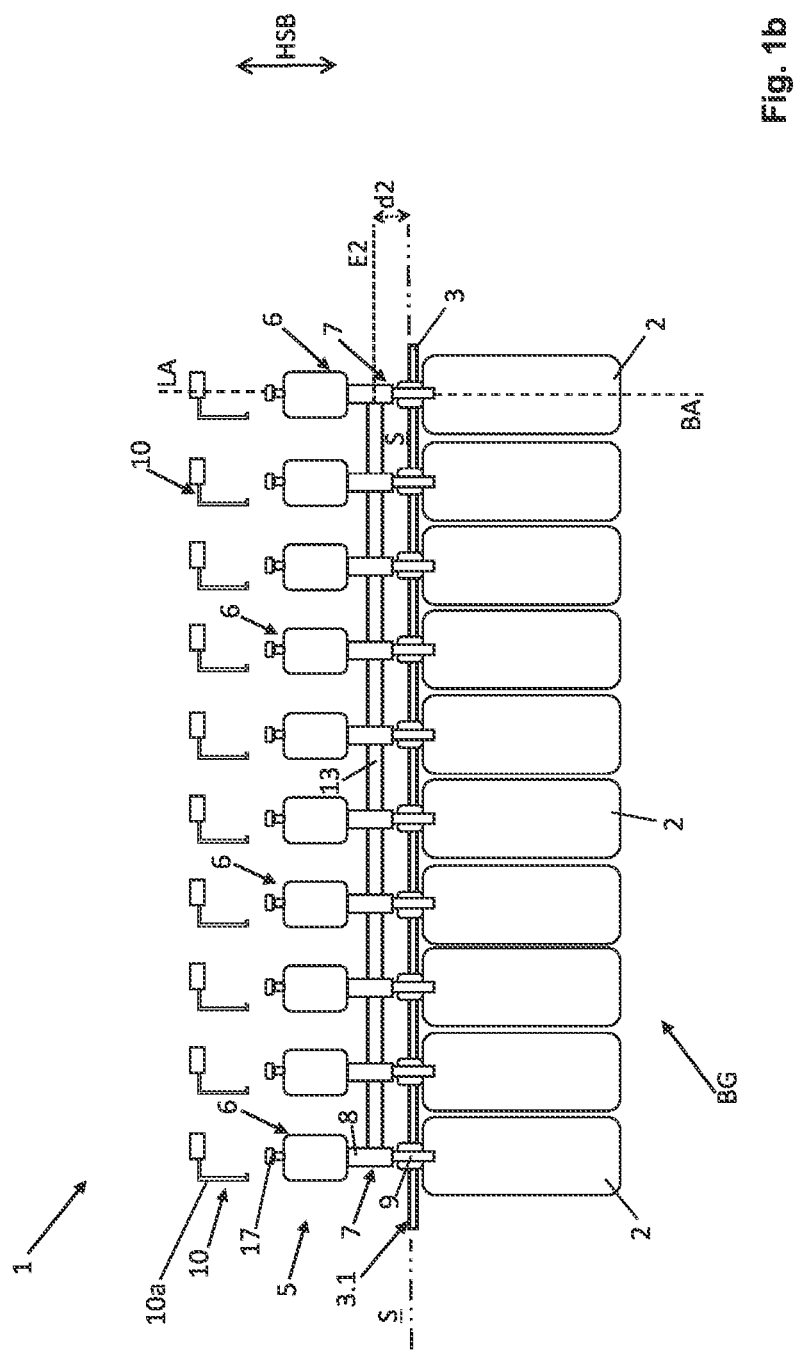

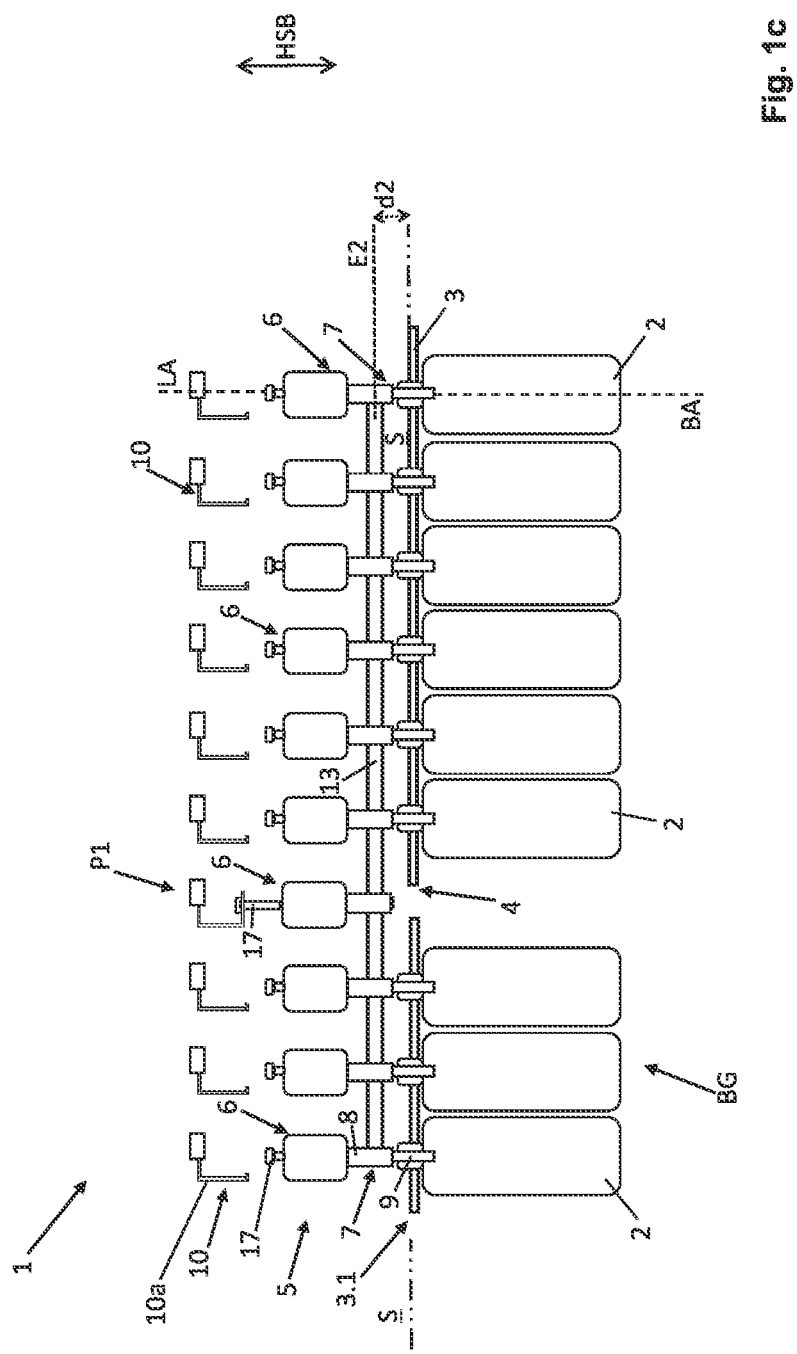

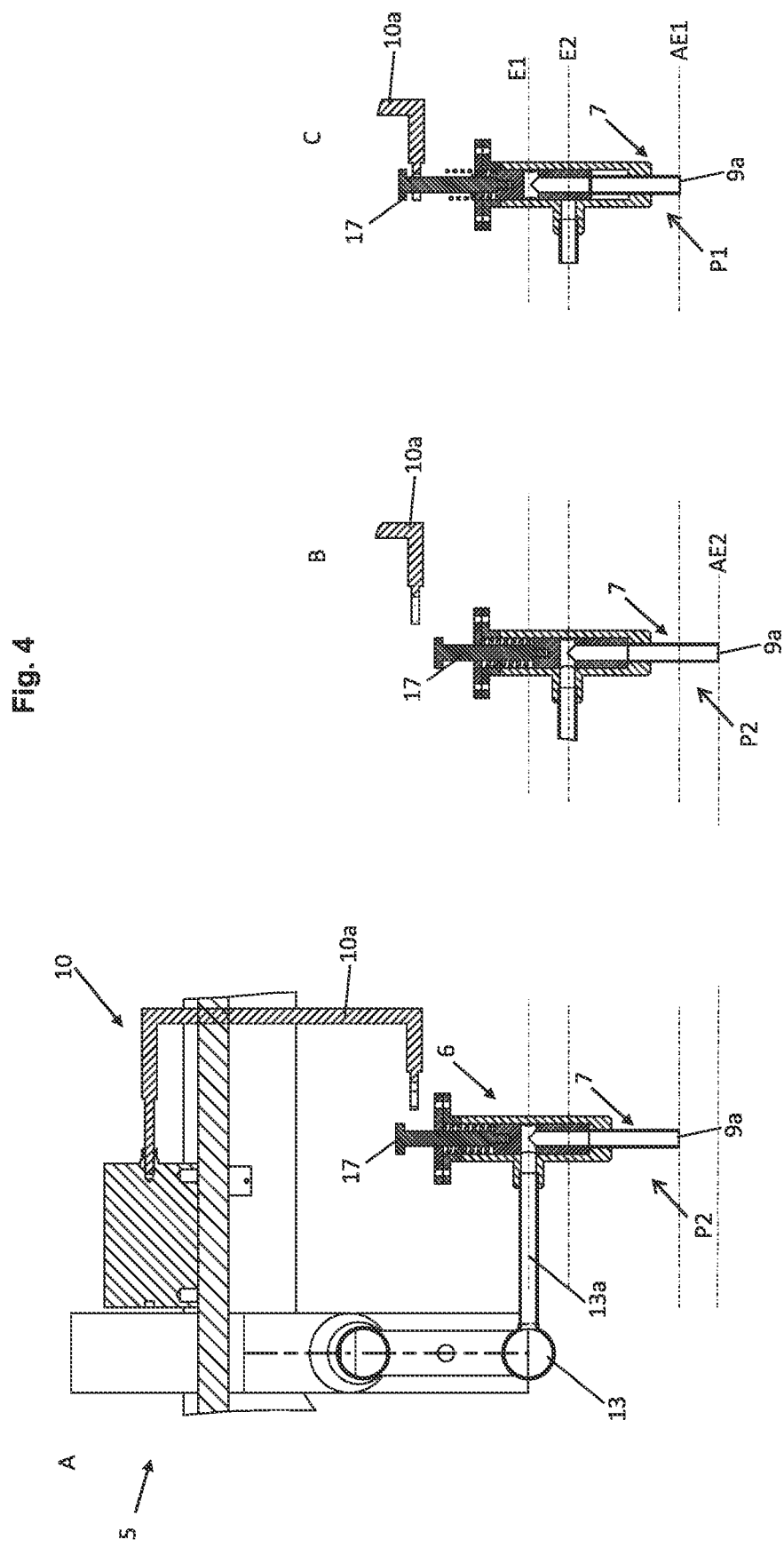

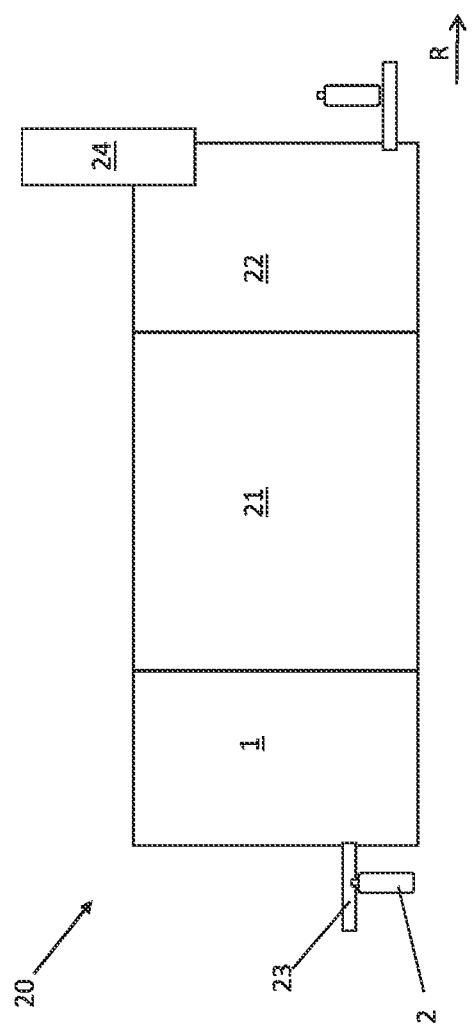

DEVICE AND METHOD FOR TREATING CONTAINERS

FIELD AND BACKGROUND OF THE INVENTION

The invention relates to an apparatus and a method for treating containers with a medium, in particular for sterilising containers, in particular containers made of plastic, such as, for example, plastic bottles, and specifically for preference in cyclic operation in the course of the sterile filling of containers with a beverage, by means of a cyclically operated linear filler, in particular an aseptic filler.

During the filling of liquid foodstuffs, in particular beverages, for hygienic considerations and for reasons relating to the storage life of the filled beverage, particular attention must be paid to the sterilisation. A precondition for the sterile filling of containers in this situation is the maintaining of sterile or aseptic conditions. Such sterile filling of the containers therefore takes place, for example, in an aseptic filling system, namely in an aseptic filler.

In this situation, the principle is already known of the still empty containers being subjected to sterilisation in preparation for the actual filling procedure, wherein, following on from this, the actual sterile filling of the containers takes place, and the beverage is filled into the sterilised containers. The filled containers are then in turn, directly following on from the filling process, closed in a closing apparatus, which as a rule is comprised in the aseptic filling system, still under sterile conditions, with container closures which are delivered to the system and likewise sterilised.

For the sterilising of bottles, cans, or similar containers, methods are known in this context with the use of sterilising media containing hydrogen peroxide ($H_2O_2$), i.e. with the use of a sterilisation medium which contains, for example, hydrogen peroxide in a mixture with hot sterile air. With this method, which is used, for example, for the sterilising of containers for beverages but also for the sterilising of containers or packages for other products, such as pharmaceuticals or medicinal products, during the introduction of the hot $H_2O_2$ sterilisation medium an $H_2O_2$ condensation film forms on the inner surface of the cooler container due to condensation, which in a following activation phase is activated by the introduction of a sterile hot gaseous and/or vaporous activating medium, for example by the introduction of hot sterile air, in such a way that the decomposition of the $H_2O_2$ leads to the formation of free acid radicals, which react with bacteria and other contamination which may be present and lead to the sterilisation of the containers. WO 01/28863 A1, for example, describes such a sterilisation method for the sterilisation of PET bottles, making use of $H_2O_2$.

The principle is also known that, with the method of sterilisation referred to, the introduction or blowing in of the $H_2O_2$ sterilisation medium and/or of the hot sterile air or of the activation medium takes place by way of corresponding treatment or sterilisation heads, which in each case are provided with an outlet or dispensing tube for dispensing the $H_2O_2$ sterilisation medium, and are also designated, for example, as gas lances. With linear machines in particular, such as linear fillers, several containers are treated simultaneously in one work cycle, wherein several gas lances, arranged in linear rows, form one unit, in particular one treatment unit or device, and blow the $H_2O_2$ sterilisation medium into several containers likewise arranged in a linear row. With such known linear machines, in particular linear fillers, which as a rule are operated cyclically or in stepped operation, the containers are transported, for example, by means of what are referred to as linear transporters, wherein such linear transporters are, in particular, also constituent parts of the corresponding container handling machines.

By means of such linear transporters as referred to, known to the person skilled in the art, the containers are moved cyclically for their treatment to different treatment stations or positions following one another in the transport direction, i.e. are moved in steps along the transport segment, preferably in the form of container groups, which comprise a plurality of containers arranged spaced apart from one another in a linear row, which are preferably held in each case suspended by a container flange. The containers of a container group are in this situation arranged relative to one another in such a way that the container longitudinal axes of the containers preferably run parallel to one another, and in each case are at the same spacing interval from one another. In this situation, the principle is likewise known of the containers being held by means of a linear holding device or container carrier, preferably by means of a carrier strip with corresponding container holders, wherein the suspended containers project upwards with their neck part, adjacent to the filling opening, above the carrier strip. Linear transporters with container carriers of the type referred to are known, for example, from WO 2013/004324 A1.

With the known apparatuses and methods, the containers which are held as a container group suspended in the carrier strip are conveyed into a corresponding sterilisation station or into an apparatus for sterilising, and are positioned beneath a treatment device, in particular beneath the gas lances, such that the dispensing of the sterilisation medium into the containers can take place, namely into the container interior, in cyclic operation. The principle is also known that an aseptic or sterile space or aseptic space is formed in the region above the carrier strip of the linear transporter, which is also designated as an aseptic zone, such that the parts of the container projecting upwards over the container strip, which comprise the filling opening or the container mouth, are located in the aseptic space, as do the sections of the outlet or dispensing tubes which comprise the respective outlet opening. For the sterilising, with the known apparatuses, next the container device with all the gas lances is moved downwards by means of a lowering movement into an operational position, in such a way that the sections of the outlet or dispensing tubes, comprising the outlet opening, immerse into the containers. Finally, the outflow of the $H_2O_2$ sterilisation medium is put into effect, such that the $H_2O_2$ sterilisation medium is blown into the interior of the containers.

With the known linear sterilisation apparatuses, driven in stepped operation, it is always the entire container group which is treated per working cycle, i.e. per working cycle all the treatment heads or gas lances are brought as a group into the operational position. The problem arises in this case that in the event of there being a container missing, i.e. if there is no container present at one of the container receivers of the carrier strip, the outlet or dispensing tube is introduced into the non-sterile space beneath the carrier strip, and, as a result, is exposed to the risk of contamination.

With aseptic filling, however, the maintaining of the aseptic zone acquires a central significance, as a result of which, according to the solutions known from the prior art, the attempt has been made heretofore to avoid possible contamination in the event of a container missing in the carrier strip by leaving the whole treatment unit or treatment device, with all the gas lances, in the upper starting position, and not lowering it into the operating position, in order to avoid possible contamination with certainty. This incurs the substantial disadvantage, however, that the containers which are present cannot be sterilised, and must be disposed of as rejects. Accordingly, despite the solutions known from the prior art, there is a need for improved devices for treating containers with medium, in particular sterilising medium.

SUMMARY OF THE INVENTION

The object of the invention is therefore to provide an apparatus for treating containers with medium, in particular sterilising medium, which avoids the disadvantages of the solutions known from the prior art, and which allows, despite a simple structural design, and with reliable maintaining of the aseptic conditions required, for the sterilising of the containers positioned in the sterilising apparatus to be ensured with full effect.

To solve this object, an apparatus for treating containers with a medium is configured in accordance with the features as claimed. Moreover, a linear filler for the aseptic filling of containers is configured in accordance with claim 15 with a corresponding apparatus, and a method is described for the treating of containers with a medium, with the features as claimed. Advantageous further embodiments of the invention are provided in the dependent claims. In this situation, all the features described are in principle the object of the invention, alone or in any desired combination, regardless of their relationship in the claims or reference to them. The claims are further deemed to be a constituent part of the description.

The present invention provides for an apparatus for the treating of containers, being transported in groups along a conveying path in cyclic operation, with a medium, in particular a gaseous, vaporous, or fluid medium. The apparatus comprises at least one linear holding device with a plurality of container holders for holding the containers in a suspended state, and comprises at least one treatment station, which comprises at least one treatment device with a supply line for the medium, as well as with a plurality of outlet heads connected to the line by means of respective branch lines. At least the outlet heads can be moved by means of a drive together as a group in the vertical direction. In this situation, each outlet head has a vertically oriented axis, and comprises an outlet line extending along the longitudinal axis for the dispensing of the medium into the container. For the treatment of the containers, the outlet line can be introduced at least in sections into the container held suspended in the container holding means. The apparatus is characterised in particular in that at least one controllable restraining mechanism is assigned to each outlet head, wherein the apparatus further comprises at least one control means which is in communicating connection with the restraining mechanism, and wherein the controllable restraining mechanism comprises at least one restraining element and is configured so as to hold at least the outlet line of a respective outlet head in a restraining position, controlled in accordance with the requirements.

"Containers" in the meaning of the invention are in particular such as are configured with a protruding container flange beneath their container opening or mouth, e.g. containers or bottles made of plastic, for example of PET.

"Medium" in the meaning of the invention is understood to signify all fluid, gaseous, or vaporous media which are suitable for the treatment of containers. For example, in this situation this may involve sterilisation means or media, cleaning means or media, drying means or media, means or media for the imposition of inert gas or tensioning gas, but also a filling product.

In the meaning of the invention, transport "along a conveying path in cyclic operation" is to be understood in particular as transport in which the transport segment formed between a container inlet and a container outlet has a straight line course at least in one part region, i.e. a linear transport of the containers. Transport takes place in a cyclic manner or in step operation.

The apparatus according to the invention can be understood as an apparatus for treating containers with a sterilising medium, and is to be understood in particular as an apparatus for the sterilising of containers, and specifically for sterilising with a sterilising medium, in particular in a known manner with a gaseous or vaporous or aerosol type sterilising medium, for example with a sterilising medium containing $H_2O_2$, which in the present case can also be designated as an $H_2O_2$ aerosol. Sterilising with a sterilising medium containing $H_2O_2$ also comprises in a known manner the use of hot sterilising medium and/or the use or additional use of hot activating medium and/or hot sterile air. In the present situation, the sterilising of the containers is to be understood in particular as a treatment step, which precedes a filling of the containers with fluid filling product under aseptic or sterile conditions, wherein such an aseptic filling takes place in an aseptic filler, in particular in an aseptic linear filler, and the apparatus according to the invention is located upstream of an aseptic filling station of an aseptic filler, or can also be configured as an integral component part of an aseptic linear filler. It is self-explanatory that a drying of the containers or a gas expulsion step falls under the treatment of containers with medium in the meaning of the invention.

The medium, in particular sterilising medium, is conveyed via a supply line and corresponding branch lines, which branch lines can also be understood as a corresponding connection distributor system branching off from the supply line, to a plurality of outlet heads of the treatment device, arranged next to one another as a group, and is dispensed via respective outlet lines, which in turn are in connection with the supply line by means of the branch lines, into the containers, and for the treatment, in particular sterilisation, is introduced into the interior of the containers. The dispensing of the sterilising medium can also be understood in this situation as an outflow of the sterilisation medium out of the outlet line, and in particular as the blowing of the sterilising medium into the container, in particular also as the imposing of sterilising medium onto the container. The outlet heads, with the respective outlet line, can in this situation be designated as lances, treatment lances, or gas or aerosol lances, or as nozzles or aerosol nozzles, or as gas or aerosol distributors or outlets, or also as spray units or spray pipes.

At least the outlet heads of the present apparatus can be moved in a vertical direction by means of a drive, wherein the vertical movement in the meaning of the invention is also to be understood as a raising and lowering movement, or as an up and down movement, and wherein, preferably, all the outlet heads of the treatment device are moved vertically together as a group by means of the raising and lowering movement. In particular, the outlet heads are moved up and down with their supply line and their branch lines or the connection distributor system respectively. The outlet heads can therefore also be designated in this situation as lifting elements.

In the meaning of the present invention, a linear holding means with a plurality of container holders is understood in particular to be a container carrier configured in a known manner, in particular as a transfer apparatus or a transporter, with which the containers are held suspended by a container flange formed beneath the container mouth at a container neck during the holding or transport. The linear holding means can be configured as a flat carrier strip in the form of a cell board, which is provided with a plurality of container holders for holding the containers as a container group, or for multi-track transport of the containers in the form of a container group, and specifically in each case with one container holder for each track of the multi-track container flow. The container holders of the carrier strip can be configured, for example, as a longitudinal slot, or preferably as individual openings.

The containers are arranged or suspended in the holding means next to one another in such a way that respective container main axes of the containers held in a holding means are oriented parallel to one another. For the treatment, in particular sterilisation, the containers suspended in the container holders of the holding means are positioned beneath the treatment device in such a way that an outlet head is assigned to each container suspended in the holding means, and the respective longitudinal axes of the outlet heads coincide with the container main axes of the assigned containers in a common vertical axis, which can also be understood as a treatment axis. In this arrangement, each outlet head, together with the assigned container holder, forms a treatment point, wherein, starting from an upper side of the container mount, an aseptic space or sterile space is formed above this, in which aseptic or sterile conditions prevail. The aseptic space is in this situation also designated as an aseptic zone or sterile zone or hygiene zone.

According to the invention, with the present apparatus the controllable restraining mechanism is assigned to each outlet head, wherein, by means of the restraining mechanism, put into effect by means of the restraining element, at least the outlet line of a respective outlet head can be held in a restraining position in a manner controlled according to requirements. The restraining position is also to be understood in this situation as a restraining position. As a result, in particular it is ensured with the apparatus that, at or after the lowering of the outlet heads, in particular at or after the lowering of the treatment apparatus, at least the outlet line, and in this situation in particular its lower section, carrying the outlet opening, is held at a higher level than in the non-restrained position, in particular even if there is no container present at a container holder of the container mount, due to an error.

For particular preference, and very particularly advantageously, the controlled restraining can take place individually and singly for each outlet unit. In this present situation, this is also to be understood as retention, in particular individual retention or individual locking. Particularly advantageously, in this situation it can be ensured that, during a lowering movement of the outlet heads or treatment device, carried out for the sterilisation, namely at the beginning of the sterilisation process, the section of the outlet line carrying the outlet opening, in particular also single individual outlet lines, always remains arranged in the aseptic space or sterile space, and is not moved into the free space, in particular non-sterile space, beneath the holding means, and, in particular, even if no container is present in a container holder of the container mount due to an error. The control means which is in communicating connection with the restraining mechanism is preferably arranged outside the aseptic zone.

In addition to this, it is advantageously possible to react to errors at individual treatment points or treatment positions, in particular to the absence of containers at individual container holders of the container mount. Advantageously, as a result of this, it is possible for the outlet line to be held back at individual unoccupied container holders, at which a container is missing, and specifically in such a way that the section of the outlet line on the free end side preferably does not immerse into the space beneath the holding means. Advantageously, in addition to this, the safety and reliability of the process can be increased, since, for example, the outlet line does not leave the hygienic zone, in particular the sterile or aseptic zone, if a container is not present. As a result, recontamination is avoided. The aseptic space above the container mount is in this situation advantageously reliably maintained.

At the same time, however, it can also be ensured that the containers which are present and being held in the holding means are treated in every case, preferably sterilised, and specifically at all the treatment positions at which a container is present. This leads to an increase in capacity by clearly more effective performance of the treatment, in particular sterilisation, since production downtime is avoided if there are no containers present, in particular at the start and end of production.

Moreover, the apparatus can be used particularly advantageously for the optimisation of the treatment process, in particular the sterilisation process, and for test purposes, since, for example, the outlet line can be individually held back in a controlled manner, such that individual steps in the treatment process can also be interrupted. It is therefore possible, for example, for a container track of the container group, or individual containers, to be treated differently, in that, for example, a lower imposition of medium takes place, sterilisation medium in particular, and/or an imposition of activating medium, and/or hot sterile air for drying, can be individually varied or interrupted or left out. Safety and reliability can also be increased, since it is possible in particular for the outlet units to be retracted more forcefully by holding back or moving inwards, and therefore avoiding overheating of the containers which are to be filled in the event of extended standstill times.

The restraining element is preferably configured in such a way as to enter into engagement in a controlled manner with coupling means provided at each outlet head and in working connection with the outlet line, wherein, by the engagement of the restraining element into the coupling means, the restraining of the outlet line is put into effect.

Preferably, the outlet line is formed by at least two parts, namely by at least one fixed tube piece and a movable outlet end piece, wherein the outlet end piece can be moved relative to the tube piece in an axial direction along the longitudinal axis, in particular vertically. The outlet end piece, which comprises the outlet opening at its free end, can adopt a retracted and extended position relative to the tube piece, in particular moved up and down, and namely extended and retracted.

In this situation, according to a further advantageous embodiment, the outlet unit is configured in telescopic form, and the outlet end piece is arranged coaxially to the tube piece, and held so as to be at least partially axially movable in the tube piece. For particular preference, the outlet end piece can be drawn in by way of the restraining mechanism, by axial movement in the vertical direction upwards from at least one extended position into the tube piece, and specifically into a restraining position which corresponds to the restrained position, wherein a longitudinal extension of the outlet line along the longitudinal axis in the extended position is greater than in the retracted restraint position. In order to hold the outlet line in the restraint position, the axial movement of the outlet end piece in the tube piece takes place in a controlled manner, and specifically initiated by the restraining mechanism, wherein the restraint element preferably engages into a coupling means which is in operational connection with the outlet end piece, and thereby holds back the outlet end piece.

For particular preference, the restraining mechanism can be actuated by means of an actuator, wherein the actuator is controlled and can take effect, for example, by rotation or in linear manner. The restraining mechanism, in particular the restraint element, can be rotated or pushed in by means of the actuator in a controlled manner, and therefore holds the outlet line, in particular the outlet end piece, beneath the holding device before the immersion into the container or into the free non-sterile space beneath the holding device.

According to a further advantageous embodiment variant, provided in each outlet head is an internal valve for the regulated dispensing of the medium, in particular a sterilising medium, wherein the internal valve, when in an opened state, clears a dispensing flow path for the medium, in particular a sterilising medium, through the outlet line, and in a closed state closes the dispensing flow path, and wherein the internal valve is, for very particular preference, arranged and configured in such a way that the dispensing flow path is closed in the restraining position of the outlet line or with the outlet end piece in the restraining position. In this situation the internal valve is preferably controlled.

It is understood that the internal valve can also be configured in alternative embodiment forms in such a way that the dispensing flow path is open in the restrained position of the outlet line or in the restraining position of the outlet end piece, and, for example in the case of a sterilising process, with an unoccupied container holder, the sterilisation medium flows into the aseptic zone or also into the non-sterile region beneath the holding means, as a result of which the effect of maintaining the aseptic zone can be additionally enhanced.

Likewise preferred is an embodiment variant in which an internal choke is provided in each outlet head, wherein the internal choke is configured and equipped in such a way that in the restraining position of the outlet line, or in the restraining position of the outlet end piece, the dispensing of the medium, in particular sterilising medium, by way of the outlet line is choked, in such a way that, in the restraining position of the outlet line or in the restraining position of the outlet end piece, a flow of the medium, in particular sterilising medium, from the outlet line is reduced. In this situation the internal choke is preferably controlled. In addition to this, it is also possible in the context of a sterilising process, at an unoccupied container holder, for the sterilising medium to flow at a reduced flow rate into the aseptic zone or even into the non-sterile region beneath the holding means. As a result, the effect of maintaining the aseptic zone can be additionally enhanced, with economical use of sterilising medium.

Preferably, the apparatus further comprises at least one sensory detection unit for detecting the presence of containers in the container holders of the container mount, wherein the sensory detection unit is in communicating connection with the control means. For particular preference, the sensory detection unit is formed in this situation by at least one optical sensor or by a location sensor. As optical sensors, use can also be made in particular of electronic cameras, light barriers, or the like.

In particular, it can be detected by means of the sensory detection unit which treatment positions are occupied or unoccupied. The corresponding measured data or signals of the sensory detection unit interacting with the control means is forwarded by means of a corresponding transfer and evaluation unit to the control means and evaluated. The control means thereupon issues control signals to the restraining means or corresponding actuators, which likewise interact with the control means, in order to hold back the outlet line, in particular the outlet end piece, at the respective unoccupied treatment positions.

The controlling of the restraining mechanism and of the internal valve or internal choke for the corresponding regulating or adjusting of the dispensing of the sterilising medium takes place preferably in a mutually co-ordinated manner.

According to a further preferred embodiment of the invention, the outlet lines, in particular the outlet lines with the associated connected branch lines and the supply, are configured to be height adjustable, in such a way that the outlet openings can be positioned at least at one predetermined height ad/or in a stepped manner at different heights above the holding means.

For example, in the event of there being no container present in a container holder, the outlet end piece can be positioned, by means of the control means and the restraining mechanism, at a height in such a way that the outlet opening is arranged in a region of approximately 0.5 mm to 5 mm above the upper side of the holding means. At the same time, the dispensing of the sterilising medium can be adjusted by the control means in such a way that the sterilising medium is introduced through the container mount into the non-sterile space, in order to ensure the maintaining of the aseptic conditions in the aseptic zone. It is also possible, in the event of there being no container present, for the dispensing of the sterilising medium through the container mount into the non-sterile space to be varied, in particular reduced.

For particular preference, the apparatus is configured as an integral machine station of an aseptic linear filler. The apparatus can be configured in particular as an apparatus for the sterilising of containers.

The invention also provides for a linear filler for the aseptic filling of containers with a fluid filling product, which comprises at least one transport apparatus for the transport of containers in a transport direction, and at least one filling station. The linear filler is operated in step operation, and comprises, as described heretofore, an apparatus arranged upstream of the filling station in the filling direction for sterilising the linear filler, for treating the containers with a medium, in particular sterilising medium.

The invention also provides for a method for treating containers being transported in groups along a conveying path in cyclic operation with a medium, in particular a sterilising medium. With the method, the containers are held suspended, by means of a linear holding means with a plurality of container mounts, in the form of an ordered container group with a predetermined number of containers, and are positioned in a treatment station of an apparatus beneath a treatment device. The treatment device comprises a supply line for the medium, and a plurality of outlet heads connected to the supply line by means of branch lines. In this situation, an outlet head is assigned to each container of the container group, wherein, with the method, the outlet heads are moved together as a group by means of a corresponding drive, by a raising and lowering movement, in a vertical direction downwards, and are thereby brought closer to the assigned containers in such a way that an outlet line provided at each outlet head for the dispensing of the medium by way of a respective container mouth is introduced at least partially into the assigned container. The method is characterised in particular by the fact that the outlet line of a respective outlet head is held back in a restraint position by means of a restraining mechanism controlled by a control means in accordance with requirements.

If a container is present in a respective container holder, and with the outlet heads in the lowered state, in particular with the treatment device lowered, the outlet line is arranged in such a way that it remains in an extended position, and, for the dispensing of the sterilising medium, is introduced at least partially into the assigned container. For particular preference, the outlet line of each individual outlet head is controlled in accordance with requirements and individually held back, for particular preference at the place where a container is missing in the container group, and therefore the container holder of the linear container mount assigned to the outlet head is unoccupied.

Preferably, a method for the sterilising of containers is provided wherein, at least in the treatment station of the apparatus, and in at least one region above the holding means, an aseptic zone is formed and maintained, and specifically at least in the region in which the container mouths are arranged of the containers which are held suspended. The outlet line is held back and controlled in accordance with requirements in such a way that the restrained outlet line in the restrained position is arranged entirely in the aseptic zone.

For further preference, the outlet line comprises at least one fixed tube piece and a movable outlet end piece, wherein, in order to adopt the restraining position of the outlet line, the outlet end piece is moved in the axial direction along the longitudinal axis of the respective outlet head, relative to the tube piece, in particular being drawn into the tube piece.

BRIEF DESCRIPTION OF THE FIGURES

The invention is explained in greater detail hereinafter on the basis of the figures in relation to exemplary embodiments. The figures show:

FIG. 1a In a greatly simplified schematic view, an embodiment of an apparatus for treating containers with sterilising medium, represented with the treatment device in a first upper height position;

FIG. 1b the view according to FIG. 1a, represented with the treatment device in a second lowered height position in normal operation;

FIG. 1c the view according to FIG. 1b, represented in operation but with a container missing at a treatment position;

FIG. 5 a greatly simplified schematic representation of an aseptic linear filler.

DETAILED DESCRIPTION OF THE INVENTION

Figure 2:
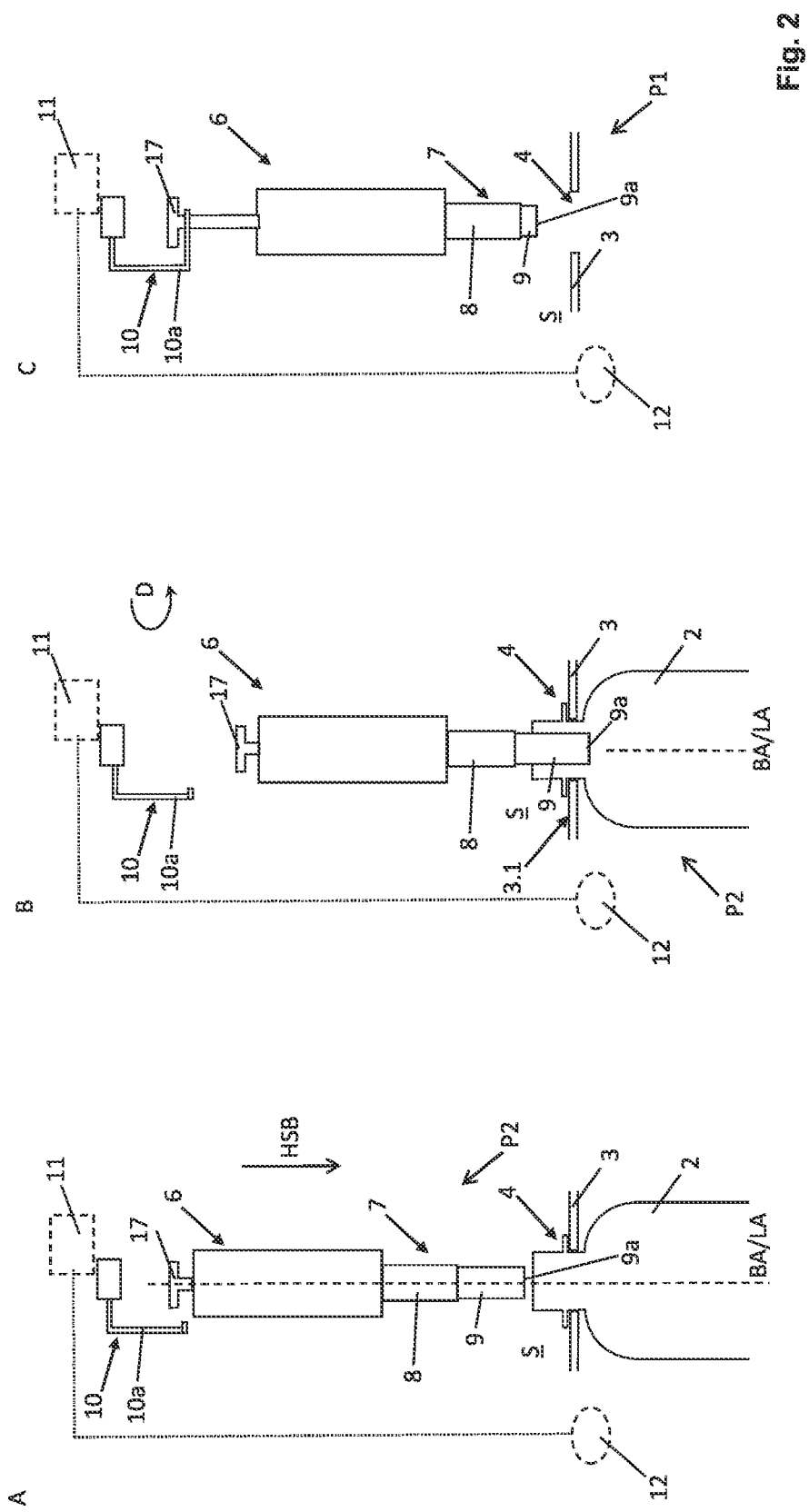
FIG. 2A-C in greatly simplified partial representations, in sections, an embodiment of the apparatus, in different operational states in each case.

The apparatus, designated in the figures in general by 1, for treating containers 2, being transported in groups along a conveying path, with a medium, in particular a sterilising medium, serves in particular for the sterilising of the containers 2, in particular of PET bottles with a sterilisation medium containing $H_2O_2$, and in this situation can also be designated as an apparatus for sterilising.

The apparatus 1 comprises a linear container mount 3, configured in a known manner, with a plurality of container holders 4 for the suspended holding of the containers 2, wherein the containers 2 are held by means of the holding means 3 as a container group BG, positioned correspondingly in the apparatus 1, and also transported further in a cyclic manner in parallel lines. In the embodiment represented by way of example in FIGS. 1a to 1c, the holding means 3 are equipped with ten container mounts 4, such that the number of the containers 2 being held and transported simultaneously of a container group BG is equal to ten. The number of containers can also be understood in this situation as a group number or group size, and at the same time corresponds in particular to the number of treatment locations or treatment positions present in the apparatus.

The suspended containers 2 are arranged next to one another in a linear row, spaced apart from one another, in such a way that respective container main axes BA of the containers 2 of a container group BG preferably run parallel to one another and in each case exhibit the same spacing interval. The containers 2 project upwards with their neck parts adjacent to the filling opening over an upper side 3.1 of the holding means 3, wherein the space above the upper side 3.1 of the holding means 3 is configured as an aseptic area S or aseptic zone, in which sterile or aseptic conditions prevail.

The apparatus 1 further comprises a treatment device 5 with a plurality of outlet heads 6, likewise arranged in a linear row at a distance interval from one another, which in the embodiment represented are likewise provided as ten in number. The outlet heads 6 comprise in each case vertically oriented longitudinal axes LA, which in turn run parallel to one another. Each outlet head 6 is assigned to a container mount of the holding means 3, and together with this forms in each case a treatment location or treatment position. The respective container main axes BA of the containers 2, suspended in the container mounts 4 and positioned for sterilising, coincide in this situation with the respective longitudinal axes LA of the assigned treatment head units 6 and form a common treatment axis.

The treatment device 5 further comprises a supply line 13 for the sterilisation medium, wherein the outlet heads 6 are connected by means of corresponding branch lines 13a (see FIGS. 3a, 3b), or by a connection distribution system, to the supply line 13. Each outlet head 6 comprises an outlet line 7, extending along the longitudinal axis LA, for dispensing the sterilisation medium into the containers 2. In the preferred embodiment of FIGS. 1a to 1c represented, the outlet line 7 comprises a fixed tube piece 8 and a movable outlet end piece 9, which comprises at its free end an outlet opening 9a (see FIG. 2). The outlet end piece 9 can be moved axially relative to the fixed tube piece 8, along the longitudinal axis LA, and in the embodiment represented is accommodated in the tube piece 8, such that the outlet line 7 is configured as telescopic in form.

The outlet heads 6 of the embodiment represented, together with their connection distributor system 13*a* and the supply line 13, are movable in the vertical direction by means of a raising and lowering movement HSB, such that, in the example from FIGS. 1*a* to 1*c*, the treatment device 5 is configured as being capable in its entirety of raising and lowering movement. The raising and lowering movement takes place by way of a drive unit, not represented in the Figures. By way of the raising and lowering movement HSB, the treatment device 5 can be moved from a first upper height position into a second lowered height position and vice-versa, wherein the first upper height position represents a transport position, in which the containers 2 can be transported during a cycle, and wherein the second lowered height position represents a treatment position, in which the containers 2 is treated with the medium, in particular having the medium imposed on it.

In the first upper height position, the treatment device 5 adopts a position in which, in the example represented, the supply line 13 comes to lie on a first height level in a first level plane E1, which runs at a first height spacing interval d1 to the upper side 3.1 of the holding means 3, as represented in FIG. 1*a*. In the second, lowered height position, the treatment device 5 adopts a position in which, in the embodiment represented, the supply line 13 comes to lie in a second level plane E2, which runs at a smaller second height distance interval d2 from the upper side 3.1 of the holding means 3, as represented in FIGS. 1*b* and 1*c*. FIG. 1*b*. FIG. 1*b* shows in this situation a normal operation, when all the container mounts 4 of the holding means 3 are engaged or occupied in each case by a container 2. FIG. 1*c* shows the apparatus in treatment operation when a container 2 is missing in a container mount 4, in FIG. 1*c* at the treatment position "four", namely at the fourth position from left, and the corresponding container mount 4 is therefore unoccupied.

Moreover, in the exemplary embodiment represented in FIGS. 1*a* to 1*c*, for each outlet head 6 a restraining mechanism 10 is provided, controlled by means of a control means 11 (see FIG. 2), with a restraining element 10*a* for holding back the outlet line 7, in particular the outlet end piece 9, in a restraining position P1, wherein the restraining position P1 in the embodiment represented can also be understood to be a restraining position.

In FIG. 1*c*, at the treatment position "four", due to the container 2 being missing, the outlet line 7 is accordingly arranged in the restraining position P1. Controlled by the control means 11 (see FIG. 2), the restraining element 10*a* is actuated or activated for this purpose in such a way that it engages into a coupling means 17 provided at the outlet head 6, which is in a working operational connection with the outlet line 7, such that the outlet line 7, initiated by the coupling means 17 which are in engagement with the restraining element 10*a*, is held back, and, as a result, even when in the second lowered height position of the treatment device 5, does not immerse into the non-sterile space beneath the holding means 3, but instead is held in its entirety inside the aseptic zone S.

With regard to FIG. 2, representations A to C, individual operating states or positions of the treatment device 5 are shown in greater detail, in particular of the outlet line 7 of the outlet heads 6.

Section A from FIG. 2 shows a state at a container mount 4, occupied by a container 2, in which the treatment device 5 adopts a first upper height position, i.e. it has not yet been lowered or moved downwards in the work cycle by means of a lowering movement HSB. This essentially represents a starting position before or at the beginning of the sterilisation process. The outlet end piece 9 is located in the extended position P2.

Section B of FIG. 2 shows the state in which the container mount 4, occupied by a container 2, in which the treatment device 5 has already been lowered or moved downwards in the work cycle by means of a lowering movement HSB, and adopts the second lowered height position. This represents essentially a treatment position during the sterilisation process. Here too, the outlet end piece 9 is also in the second extended position P2, such that the longitudinal extension of the outlet line 7 is perceptively greater than the axial length of the tube piece 8. The outlet end piece 9 in this situation is introduced via the container mouth into the container 2. The dispensing of the sterilisation medium via the outlet opening 9*a* takes place in a controlled manner, in that, by means of the control means 11, an opening of an internal valve in the treatment head 6 is initiated. The restraining mechanism 10 does not engage, since by way of the sensory detection unit 12 the presence of a container 2 at the treatment point has been detected.

Section C in FIG. 2 shows the state with an unoccupied container mount 4, in which, by means of the sensory detection unit 12, the absence of a container 2 at the treatment point is detected. In this situation, initiated by the control means 11, the restraining mechanism 10 engages, such that, despite the treatment device 5 already being lowered or moved downwards, the outlet end piece 9 is held back in the restraining position P1 in a controlled manner. The outlet opening 9*a* of the outlet end piece 9 in this situation is arranged as before inside the aseptic space S, such that contamination of the outlet end piece 9 is avoided. In this position it is possible, depending on the configuration and the application situation, the dispensing of the sterilisation medium can be adjusted in a controlled manner by way of the outlet opening 9*a*, and specifically in such a way that dispensing of the sterilisation medium into the aseptic space S or into the non-sterile space beneath the holding means 3 takes place with a full or choked volume flow, or no dispensing takes place.

In the example represented in FIG. 2, the restraining element 10*a* of the restraining mechanism 10 can be rotated by means of an actuator by a rotational movement D in such a way that it comes into engagement with the coupling means 17, which in turn is in working connection with the outlet line, in particular with the outlet end piece 9, such that, at the lowering of the treatment device 5 by the raising and lowering movement HSB, the axial movement of the outlet end piece 9 into the tube piece 8 is implemented, and the outlet end piece 9 is held back in the restraining position P1. As an alternative, however, it is also conceivable that the restraining mechanism 10 engages by way of a linear movement.

The examples described in the Figures heretofore have it in common that the outlet line 7 is configured in two parts in telescopic form, and the restraining position P1 can be incorporated in the tube piece 8 by a displacement movement of the outlet end piece 9. It is understood that this situation can of course also include alternative embodiments which are not represented in the Figures. For example, the outlet line 7 could be configured in the form of a folding bellows element, wherein, in a controlled manner, a certain deformation of the folding bellows outlet line 7 is incurred, and specifically by the engagement of the restraining element 10*a* into the coupling means 17 which are in working connection with the folding bellows outlet line 7. It is also conceivable for the entire outlet line 7 to be withdrawn into the outlet head 6. It is likewise possible, provided that a flexible supply line 13 and a flexible connection distributor system 13a allows for this, for the entire outlet head 6, together with the outlet line 7, to be held back at a higher height position.

Figure 3B:
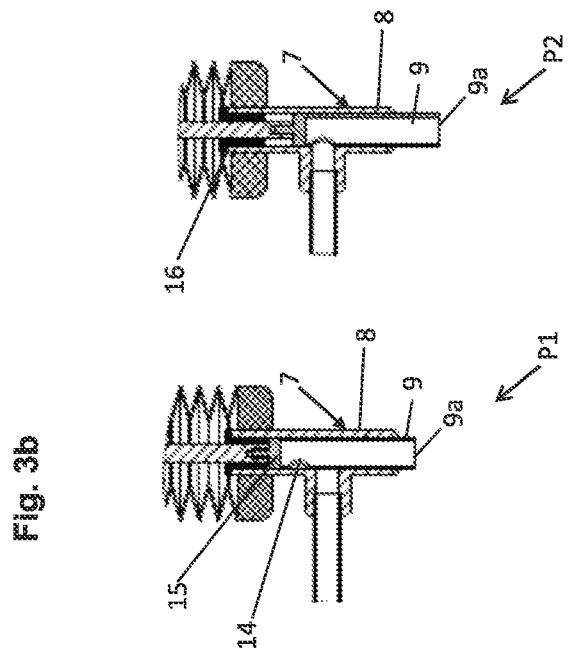
FIG. 3b in section, a partial representation of the outlet unit of the treatment head unit from FIG. 3a, and FIG. 4A-C a section through an embodiment of the treatment device, and, in section, partial representations of this.
Figure 3A:
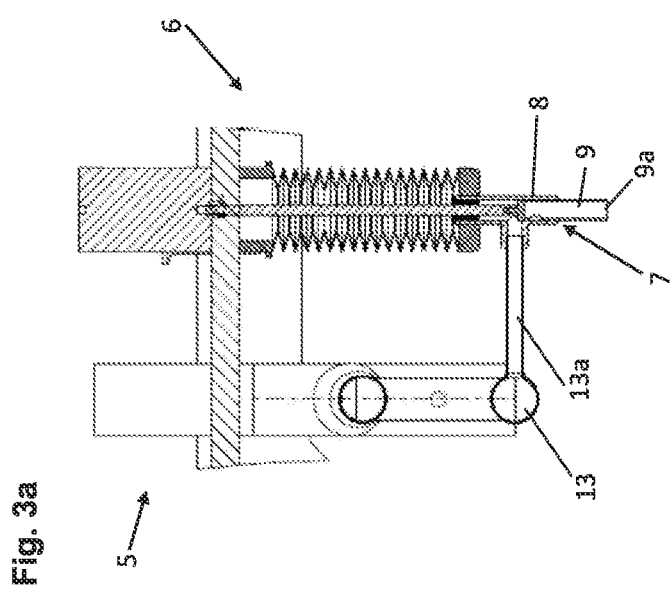
FIG. 3a a section through an embodiment of the treatment device.

FIGS. 3a and 3b, as well as FIG. 4, show as part sections, in each case in a sectional view, further embodiment variants of the apparatus 1, in particular the region of the outlet head 6 with the outlet line 7 and restraining mechanism 10. In the variant represented in FIGS. 3a and 3b, the displacement movement of the outlet end piece 9 relative to the tube piece 8 takes place in a controlled manner by means of an actuator motor, which is arranged outside the aseptic zone S and actuates a cylinder 15 or punch, which is connected to the outlet end piece 9. By the actuation of the cylinder 15, the outlet end piece 9 can be retracted or extended in the vertical direction. In this case, the cylinder 15 serves simultaneously as coupling means for the interaction with the restraining mechanism 10. In this embodiment variant, the outlet end piece 9 therefore also serves as a setting means for the internal valve.

The outlet end piece 9 comprises a passage opening 14, which in the extended position P2 according to FIG. 3b is arranged in such a way that a dispensing flow path for the sterilisation medium of the connection distributor system 13a is opened by way of the outlet line 7. In the restraining position P1, the dispensing flow path is closed. In addition, seals 16 are provided, which seal the dispensing flow path.

As can be seen from FIG. 3a, in the variant represented, it is possible, even with a position still further extended of the outlet end piece 9, for the dispensing flow path to be closed again, in that the passage opening 14 is brought into a further closing position.

Represented once again in detail in FIG. 4 is the restraining of the outlet line 7. In the section A of FIG. 4, the treatment device 5 is arranged in the first higher height position, and the supply line 13 comes to lie on the first height level in the first level plane E1. In this situation, the outlet opening 9a of the outlet line 7, which is located in the extended position P2, is located in a first outlet plane AE1. In the sections B and C, the treatment device 5 is arranged in the second, lowered height position, and the supply line 13 comes to lie on the second height level in the second level plane E2. Section B shows, in this situation, the extended position P2 of the outlet line 7, such that the outlet opening 9a in the lowered height position of the treatment device 5 is located on a second lower outlet plane AE2. Section C shows, conversely, the restraining position P1 of the outlet line 7, whereby the outlet opening 9a is also located in the lowered height position of the treatment device 5 in the first outlet plane AE1.

The restraining is put into effect by means of the restraint element 10a of the restraining mechanism 10, which comes into engagement in a controlled manner with the coupling means 17. The coupling means 17, in the embodiment represented, are configured in the form of a punch or stamp, and are connected to the outlet line 7. As a result of the corresponding engagement of the restraining element 10a in the coupling means 17, before and during the lowering of the treatment device 5, an outlet line 7 of a corresponding outlet head 6, or the outlet lines 7 of a plurality of outlet heads 6, can be held back individually, controlled in accordance with requirements. In the example represented in FIG. 4, the dispensing flow path in the extended position P2 is cleared and open (section a and B) and is closed in the restraint position P1 (section C). It is self-explanatory that, as an alternative, other control and/or switching variants are possible for the dispensing flow path.

FIG. 5 shows, in a rough schematic form, a linear filler 20 being operated in step operation for the aseptic filling of containers 2 with a liquid filling product. The linear filler 20 comprises a filling station 21 and a transport apparatus 23 for the cyclic transport of the containers 2 in a transport direction R. Provided in the transport direction R upstream of the filling station 21 is an apparatus 1 for sterilising the containers 2, which, as a part of the linear filler 20, forms a container sterilising station comprised within this linear filler. The linear filler further comprises, in the transport direction R, downstream of the filling station 21, a closing station 22, to which, by way of a container closure supply 24, sterilised container closures are supplied, and which closes the containers 2, filled under aseptic conditions, likewise under aseptic conditions.

REFERENCE NUMBER LIST

1 Apparatus for treating containers
2 Container
3 Linear holding means
3.1 Upper side
4 Container mount
5 Treatment device
6 Outlet head
7 Outlet line
8 Tube piece
9 Outlet end piece
9a Outlet opening
10 Restraining mechanism
10a Restraining element
11 Control means
12 Sensory detection unit
13 Supply line
13a Branch lines and connection distributor system
14 Passage opening
15 Cylinder
16 Seal
17 Coupling means
20 Linear filler
21 Filling station
22 Closing station
23 Transport apparatus
24 Container closure supply
AE1 First outlet plane
AE2 Second outlet plane
BA Container main axis
BG Container group
D Rotational movement
d1 First height distance interval
d2 Second height distance interval
E1 First level plane
E2 Second level plane
HSB Raising and lowering movement
LA Longitudinal axis
P1 Restraining position
P2 Extended position
S Aseptic space

The invention claimed is:

1. An apparatus for treating containers with a medium, wherein the containers are transported in groups along a conveying path in cyclic operation, the apparatus comprising:

at least one linear holding device with a plurality of container mounts for a suspended holding of the containers;

at least one treatment station having at least one treatment device with a supply line for the medium, and a plurality of outlet heads connected to said supply line by way of respective branch lines;

a drive unit configured to move said outlet heads in common as a group in a vertical direction;

each of said outlet heads having a vertically oriented longitudinal axis and an outlet line, extending along the longitudinal axis and connected to said supply line by way of said branch line, for dispensing the medium into the containers;

wherein, for treating the container, said outlet line is configured to be introduced, at least partly, into the container that is being held suspended in said container mount;

a controllable restraining mechanism assigned to each of said outlet heads and a controller in communicating connection with said restraining mechanism; and said controllable restraining mechanism including a restraining element and being configured to selectively, and as required, hold back said outlet line of a respective said outlet head in a restraining position.

2. The apparatus according to claim 1, wherein said restraining mechanism of each individual said outlet head is individually controllable.

3. The apparatus according to claim 1, wherein said restraining element is configured to enter into engagement in a controlled manner with a coupling device at each outlet head and into an operative connection with said outlet line and wherein an engagement of said restraining element into said coupling device effects a restraining of said outlet line.

4. The apparatus according to claim 1, wherein said outlet line comprises a fixed tube piece and a movable outlet end piece with an outlet opening, wherein said outlet end piece is movable in an axial direction along the longitudinal axis of the respective outlet head relative to said tube piece, and wherein, in order to hold back said outlet line, an axial displacement movement of said outlet end piece relative to said tube piece takes place in a controlled manner by way of said restraining mechanism.

5. The apparatus according to claim 4, wherein said outlet line is a telescopic line and said outlet end piece is arranged coaxially with said tube piece and is held at least partially in said tube piece so as to be axially movable.

6. The apparatus according to claim 5, wherein said outlet end piece is to be drawn in by way of said restraining mechanism by axial displacement in the vertical direction upwards from an extended position into said tube piece, and specifically into a redrawn position that corresponds with the restraining position, wherein a longitudinal extension of said outlet line along the longitudinal axis in the extended position is greater than in the restraining position.

7. The apparatus according to claim 1, wherein said restraining mechanism is configured for actuation by an actuator in rotation or linear translation.

8. The apparatus according to claim 1, wherein an internal valve is disposed in each outlet head for a controlled dispensing of the medium via said outlet opening, wherein said internal valve, in an opened state, allows for a free dispensing flow path for the medium through said outlet line, and in a closed state closes the dispensing flow path.

9. The apparatus according to claim 8, wherein said internal valve is configured to close the dispensing flow path in the restraining position of said outlet line.

10. The apparatus according to claim 1, further comprising an internal choke in each said outlet head, said internal choke being configured to choke a dispensing of the medium via said outlet line in the restraining position to thereby reduce a flow of the medium through said outlet line in the restraining position.

11. The apparatus according to claim 1, further comprising at least one sensory detection unit for detecting a presence of containers in the container mount of said holding device, said sensory detection unit being in communicative contact with said controller.

12. The apparatus according to claim 11, wherein said sensory detection unit comprises at least one optical sensor or by a position sensor.

13. The apparatus according to claim 1, wherein said outlet lines with the connected branch lines and the supply line are configured to be height-adjustable to enable a positioning of said outlet openings at at least one predetermined height and/or in a stepped manner at different heights above said holding device.

14. The apparatus according to claim 1, configured as an integral machine station of an aseptic linear filler and/or as an apparatus for sterilizing containers.

15. A linear filler for aseptically filling containers with a liquid filling product, the linear filler comprising:

at least one transport apparatus transporting the containers in a given transport direction and at least one filling station, wherein the linear filler is operated in stepped operation; and an apparatus according to claim 1, arranged in the transport direction upstream of said at least one filling station, and forming a container sterilization device of the linear filler.

16. A method of treating containers that are transported in groups along a conveying path in cyclic operation with a medium, the method comprising:

providing a treatment device with a supply line for the medium and a plurality of outlet heads connected by branch lines to the supply line;

holding the containers suspended by a linear holding device with a plurality of container mounts in an ordered container group with a predetermined number of containers and positioning the containers in a treatment station of an apparatus beneath the treatment device, wherein an outlet head is assigned to each container of the container group;

moving the outlet heads downwards as a group together by a corresponding drive unit with a lowering stroke movement in the vertical direction, and thereby bringing the outlet heads close to the respectively assigned containers, in such a way that an outlet line provided at each outlet head and connected by the branch line to the supply line, is introduced, for dispensing the medium by way of a respective container mouth, at least partially into the assigned container; and selectively, if required, holding back the outlet line of a respective outlet head in a restraining position by a restraint mechanism under control of a controller.

17. The method according to claim 16, wherein each outlet line is held back individually in the restraining position and controlled in accordance with requirements.

18. The method according to claim 16, which comprises holding the outlet line in the restraining position at a given location at which a container is missing from the container group and, due to the missing container, the container mount of the linear holding device assigned to the respective outlet head is unoccupied at the given location.

19. The method according to claim 16, wherein the method is for sterilizing of containers, and wherein, at least in the treatment station of the apparatus, an aseptic zone is formed and maintained at least in a region above the holding device, and specifically at least in the region in which the container mouths of the suspended containers are arranged, wherein the outlet line is held back selectively and under control according to requirements such that outlet line retracted in the restraining position is arranged entirely in the aseptic zone.

20. The method according to claim 16, wherein the outlet line comprises at least one fixed tube piece and a movable end piece, and wherein the method comprises, in order to adopt the restraining position of the outlet line, moving the end piece in the axial direction along the longitudinal axis of the respective outlet head relative to the tube piece.

* * * * *